United States Patent [19]

Imamura et al.

[11] Patent Number: 5,665,597

[45] Date of Patent: Sep. 9, 1997

[54] BACTERIUM KB2

[75] Inventors: Takeshi Imamura, Chigasaki; Tetsuya Yano, Isehara, both of Japan

[73] Assignee: Canon Kabushiki Kaisha, Tokyo, Japan

[21] Appl. No.: 566,541

[22] Filed: Dec. 4, 1995

[30] Foreign Application Priority Data

Dec. 2, 1994 [JP] Japan .................. 6-299323

[51] Int. Cl.$^6$ .................................................. C12N 1/20
[52] U.S. Cl. .................................. 435/253.3; 435/874
[58] Field of Search ........................... 435/240.1, 243, 435/252.1, 252.34, 253.3, 874

[56] References Cited

U.S. PATENT DOCUMENTS

| 4,562,156 | 12/1985 | Isbister et al. | 435/253.3 |
|---|---|---|---|
| 4,877,736 | 10/1989 | Fliermans | 435/183 |
| 4,925,802 | 5/1990 | Nelson et al. | 435/262 |
| 5,063,160 | 11/1991 | Holmes | 435/253.3 |
| 5,559,029 | 9/1996 | Tyndall | 435/874 |
| 5,571,716 | 11/1996 | Jones et al. | 435/253.3 |
| 5,578,474 | 11/1996 | Focht et al. | 435/874 |

FOREIGN PATENT DOCUMENTS

| 2-92274 | 4/1990 | Japan . |
|---|---|---|
| 2-273559 | 11/1990 | Japan . |
| 3-292970 | 12/1991 | Japan . |
| 6-70753 | 3/1994 | Japan . |
| 6-227769 | 8/1994 | Japan . |

OTHER PUBLICATIONS

Nelson et al., "Aerobic Metabolism . . . Isolate", Appl. & Envir. Micro., vol. 52, No. 2, Aug. 1986, pp. 383–384.

Nelson et al., "Biodegradation of Trichloroethylene . . . Pathway", Appl. & Envir. Micro., vol. 53, No. 5, May 1987, pp. 949–954.

Wackett et al., "Degradation of Trichloroethylene . . . *Pseudomonas putida* F1", Appl. Envir. Micro., vol. 54, No. 7, Jul. 1988, pp. 1703–1708.

(List continued on next page.)

*Primary Examiner*—Thomas G. Wyse
*Attorney, Agent, or Firm*—Fitzpatrick, Cella, Harper & Scinto

[57] ABSTRACT

A biologically pure culture of *Pseudomonas alcaligenes* KB2 (Deposition No. FERM P-14644) which can decompose at least one of aromatic compounds and haloorganic compounds, and a process utilizing this strain to decompose these compounds, and a process for remedying environment polluted with these compounds utilizing this microorganism.

1 Claim, 11 Drawing Sheets

OTHER PUBLICATIONS

Little et al., "Trichloroethylene Biodegration . . . Bacterium", Appl. & Envir. Micro., vol. 54, No. 4, Apr. 1988, pp. 951–956.

Tsien et al., "Biodegradation . . . OB3b", Appl. Envir. Micro., vol. 55, No. 12, Dec. 1989, pp. 3155–3161.

Wackett et al., "Survey of Microbial . . . Bacteria", Appl. & Envir. Micro. vol. 55, No. 11, Nov. 1989, pp. 2960–2964.

Kamath et al., "New Pathway . . . niger", Appl. & Envir. Micro., vol. 56, No. 1, Jan. 1990, pp. 275–280.

Harker, et al., "Trichloroethylene . . . JMP134", Appl. & Envir. Micro., vol. 56, No. 4, Apr. 1990, pp. 1179–1181.

Vandenbergh et al., "Metabolism of Volatile . . . *Pseudomonas fluorescens*", Appl. & Envir. Micro,m vol. 54, No. 10, Oct. 1985, pp. 2578–2579.

Vannelli et al., "Degradation of Halogenated Aliphatic . . . europea", Appl. & Envir. Micro., vol. 56, No. 4, Apr. 1990, pp. 1169–1171.

Henry et al., "Influence of Endogenous . . . Groundwater Aquifier", Appl. & Envir. Microb., vol. 57, No. 1, Jan. 1991, pp. 236–244.

Sandt et al., "Mobilization of the . . . in Drinking Water", Appl. & Envir. Micro., vol. 57, No. 1, Jan. 1991, pp. 194–200.

Ewers et al., "Selection of . . . by TCE", Arch. Microbiol., vol. 154, No. 4, pp. 410–413 (1990).

Journal of Japan Sewage Works Association, vol. 24, No. 273, 1987/2, pp. 27–33.

Intern. Journal of Syst. Bacteriology, vol. 39, No. 3, pp. 369–371, Jul. 1989.

Winter et al., "Efficient Degradation . . . *E. coli*", Bio. Technology, vol. 7, Mar. 1989, pp. 282–285.

Beam et al., "Microbiol. Degradation . . . Commensalim", J. Gen. Microbiol., vol. 82, Part 1, May 1974, pp. 163–169.

Negoro et al., "Growth of Microalgae . . . and $NO_x$", Appl. Biochem. and Biotech., vols. 28/29, 1991, pp. 877–886.

Uchiyama et al., "Aerobic Degradation of . . . Strain M", Agr. Biol. Chem. 53 (11), 2903–2907, 1989.

Nakajima et al., "Novel Metabolite . . . Pathway", Biosci., Biotech. Biochem., 56(3), 486–489, 1992.

Nakajima et al., "Purification and Properties . . . Methylocystis", Biosci. Biotech. Biochem., 56 (5), 736–740 (1992).

BACTERIUM KB2

BACKGROUND OF THE INVENTION

1. Field of the Invention

The present invention relates to a novel bacterial strain, a process for degrading at least one of aromatic compounds such as phenol, cresol, etc., and halogenated organic compounds, such as trichloroethylene (TCE), dichloroethylene (DCE), etc. using the microorganism, and process for remedying polluted environment, in particular, soil, sewage, waste water, and gases containing aromatic compounds or halogenated organic compounds.

2. Related Background Art

In recent years, environmental pollution with chloroorganic compounds, which are harmful to living things and difficult to decompose, has become a major problem. In particular, the soil in the manufacturing area of the paper and pulp industry, or the precision machinery and related industries is considered to be polluted with aromatic compounds, such as phenol, cresol etc., and chloroorganic compounds, such as chlorinated aliphatic compounds, for example, trichloroethylene (TCE), dichloroethylene (DCE), etc. In fact, reports on environmental investigation have revealed that such compounds are detected.

It is supposed that the chloroorganic compounds in soil are dissolved in groundwater etc. via rainwater etc. to spread all over the area.

There is a suspicion that these compounds are carcinogenic, and these compounds are quite stable in environment, so that the pollution of groundwater which is used as a source of drinking water has become a social problem.

As described above, removing the chloroorganic compounds and purifying groundwater by decomposition is an important problem in view of the protection of environment, and the various purification technologies have been developed.

For example, absorption treatment using activated carbon and decomposition treatment using radiation or heat have been attempted. The costs and/or the operations of these treatments, however, are not practical.

On the other hand, it has been reported recently that some microorganisms are capable of decomposing volatile chloroorganic compounds which are stable in environment, such as TCE, and the study of utilizing them in practice has already been started. This technique is called bioremediation, and has the following advantages:

(1) By using appropriate microorganisms, chloroorganic compounds can be decomposed into harmless substances.

(2) In principle, no special chemicals are required.

(3) The labor and cost of maintenance can be reduced.

(4) Even the chloroorganic compounds of low concentration can be completely decomposed and removed.

As the study of such bioremediation for practical use progresses, microorganisms powerfully decompose aromatic compounds and volatile chloroorganic compounds in the soil, which are the core of the technique, are strongly required.

Vacuum abstraction, for example, is a conventional method at present for removing volatile chloroorganic compounds in soil. In this method, first an abstraction well is dug, and then such compounds are sucked and removed from the soil using a suction pump. The extracted compounds, however, still exist in the gas phase, being undecomposed. In other words, the pollutant is merely moved from the soil to the gas phase, leaving the serious problem that volatile chloroorganic compounds remains even after the abstraction. This is not only the problem of soil pollution but that of air pollution as well. Polluted air includes, for example, the air polluted with volatile chloroorganic compounds generated in the plants of the high technology industry. Such polluted air must not be released into the atmosphere or environment unless it undergoes some proper treatment to remove the volatile chloroorganic compounds.

At present, the liquefaction treatment and the adsorption treatment with activated carbon are known as the methods for removing volatile chloroorganic compounds in gas phase. Adsorption treatment, however, still has the problem of regeneration of the used activated carbon. Liquefaction treatment also has some problems when it is applied to the treatment of volatile chloroorganic compounds. That is, the treatment is inefficient because of the low concentration of the pollutant in gas phase, in addition, it requires a large-scale equipment resulting in high cost. Furthermore, these treatments are not the true solution to the pollution problem because they merely remove volatile chloroorganic compounds, but do not decompose them. Thus, strongly needed are measures excellent in operation, low in cost, and enabling the complete degradation of volatile chloroorganic compounds into harmless substances.

As such bioremediation technique, for example, the practical use of a bioreactor for gas phase pollution, has been developed, microorganisms having a powerful decomposing activity toward the volatile chloroorganic compounds in soil, the core of the technique, are more and more required.

At present, almost all the microbial strains studied for the bioreactor to decompose the volatile chloroorganic compounds in gas phase, are methane producing bacteria. These bacteria require methane or methanol when decomposing volatile chloroorganic compounds. The presently known strains are not satisfactory in practice from the viewpoint of gas phase treatment or pollutant decomposition, and novel ones are needed.

The examples of isolated microorganisms capable of decomposing a volatile chloroorganic compound are given as follows. As known TCE decomposing strains are, for example, *Welchia alkenophila* sero 5 (U.S. Pat. No. 4,877, 736, ATCC 53570), *Welchia alkenophila* sero 33 (U.S. Pat. No. 4,877,736, ATCC 53571), Methylocystis sp. strain M (Agric. Biol. Chem., 53, 2903 (1989), Biosci. Biotech. Blochem., 56, 486 (1992), ibid. 56, 736 (1992)), *Methylosinus trichosporium* OB3b (Am. Chem. Soc. Natl. Meet. Dev. Environ. Microbiol., 29, 365(1989), Appl. Environ. Microbiol., 55, 3155 (1989), Appl. Blochem. Biotechnol., 28, 877 (1991), Japanese Laid-Open Patent Application No. 2-92274, Japanese Laid-Open Patent Application No. 3-292970), Methylomonas sp. MM2 (Appl. Environ. Microbiol., 57, 236 (1991)), *Alcaligenes denitrificans* ssp. xylosoxidans JE75 (Arch. microbiol., 154, 410 (1990)), *Alcaligenes eutrophus* JMP134 (Appl. Environ. Microbiol., 56, 1179 (1990)), *Mycobacterium vaccae* JOB5 (J. Gen. Microbiol., 82, 163 (1974), Appl. Environ. Microbiol., 54, 2960 (1989), ATCC 29678), *Pseudomonas putida* BH (Journal of Japan Sewage Work Assosiation, 24, 27 (1987)), Acinetobactor sp. strain G4 (Appl. Environ. Microbiol., 52, 383 (1986), ibid. 53, 949(1987), ibid. 54, 951 (1989), ibid. 56, 276(1990), ibid. 57, 193 (1991), U.S. Pat. No. 4,925,802, ATCC 53617, this strain was originally classified as *Pseudomonas cepacia* then classified into Acinetobactor sp.), *Pseudomonas mendocina* KR-1 (Bio/Technol., 7, 282

(1989)), *Pseudomonas putida* F1 (Appl. Environ. Microbiol., 54, 1703 (1988), ibid. 54, 2578 (1988)), *Pseudomonas fluorescens* PFL12 (Appl. Environ. Microbiol., 54, 2578 (1988)), *Pseudomonas putida* KWI-9 (Japanese Laid-Open Patent Application No. 6-70753), *Pseudomonas cepacia* KK01 (Japanese Laid-Open Patent Application No. 6-227769), Pseudomonas sp. (Japanese Laid-Open Patent Application No. 2-273599), *Nitrosomonas europaea* (Appl. Environ. Microbiol., 56, 1169 (1990)), *Lactobacillus vaginalis* sp. nov (Int. J. Syst. Bacteriol., 39, 368 (1989), ATCC 49540) and so on.

Among these known strains which are capable of decomposing pollutants, however, no strain meets the above mentioned conditions necessary in practical use for decomposing aromatic compounds and volatile chloroorganic compounds nor has an adequate decomposing activity.

When considering the decomposition treatment of liquid wastes containing TCE, for example, microorganisms applicable to such treatment must be able to grow and maintain their decomposing activity even in such poor surroundings as the waste water.

It is essential that new microorganisms used for such biological clarification treatment have an adequate decomposing activity to volatile chloroorganic compounds and in addition, preferably they have growth conditions different from those of known microbial strains so as to be applicable to a wider field and in more various ways.

SUMMARY OF THE INVENTION

In view of the above problems, an object of the present invention is to provide a novel microorganism capable of degrading at least one of aromatic compounds and haloorganic compounds effectively.

Another object of the present invention is to provide a process for decomposing at least one of aromatic compounds and haloorganic compounds with the novel microorganism.

Another object of the present invention is to provide a process for remedying the environment, such as soil, sewage, treatment water, groundwater or gas, polluted with pollutant containing at least one of aromatic compounds and haloorganic compounds.

According to an aspect of the present invention there is provided a biologically pure culture of *Pseudomonas alcaligenes* KB2, identified under Deposition No. FERM P-14644 in National Institute of Bioscience and Human Technology, Agency of Industrial Science and Technology.

According to an aspect of the present invention there is provided a process for decomposing at least one of aromatic compounds and haloorganic compounds using a microorganism, comprising the step of:

bringing the above microorganism of into contact with at least one of aromatic compounds and haloorganic compounds which are to be decomposed.

According to an aspect of the present invention there is provided a process for remedying environment polluted with at least one of aromatic compounds and haloorganic compounds, comprising the step of:

bringing the above microorganism into contact with the polluted environment to decompose at least one of the aromatic compounds and haloorganic compounds for the purpose of purifying the environment.

DETAILED DESCRIPTION OF THE PREFERRED EMBODIMENT

Figure 1:
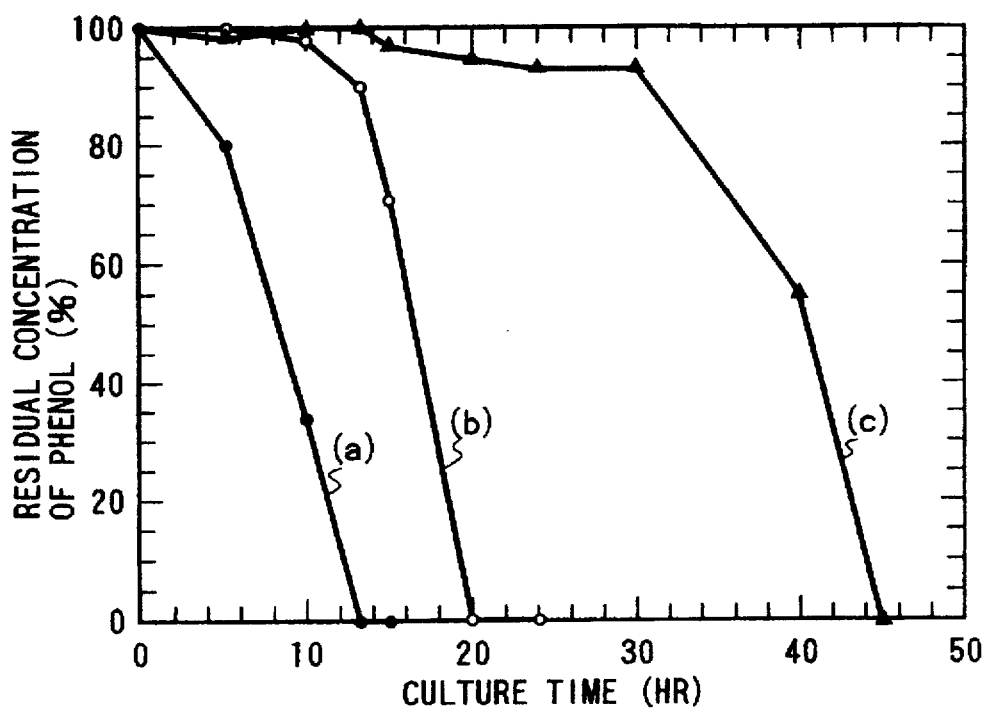
FIG. 1 is a graph showing the relations between the culture period and the concentration of phenol in the presence of KB2 strain.

The present inventors searched novel microorganisms capable of decomposing aromatic compounds or haloorganic compounds and found a novel bacterial strain capable of decomposing aromatic compounds and haloorganic compounds of high concentration in the soil polluted with volatile chloroorganic compounds. In addition, the present inventors have established a process for decomposing aromatic compounds or haloorganic compounds in a polluted aqueous or gaseous medium such as groundwater and air, wherein the above strain is brought into contact with the medium polluted with at least one of aromatic compounds and haloorganic compounds.

The novel bacterial strain of the present invention is a gram-negative rod and has the following microbiological properties:

A. growth on agar media
Standard agar: good
MacConkey agar: good
B. optimum growth temperature: 25° C.>35° C.
growth at 42° C.: good
C. physiological properties
aerobic/anaerobic: aerobic
TSI (slant/butt): alkali/alkali, $H_2S(-)$
catalase: positive
oxidation/fermentation test: –/–
reduction of potassium nitrate: positive
production of indole from L-tryptophan: negative
acidification of glucose: negative
arginine dihydrase: negative
urease: negative
esculin hydrolysis (β-glucosidase): negative
gelatine hydrolysis (protease): negative
β-galactosidase: negative
cytochrome oxidase: positive
D. assimilation of sugars, organic acids, etc.
glucose: negative
L-arabinose: negative
D-mannose: negative
D-mannitol: negative
N-acetyl-D-glucosamine: negative maltose: negative
potassium gluconate: positive
n-caprate: negative
adipic acid: positive
dl-malic acid: positive
sodium citrate: negative
phenyl acetate: negative The strain of the present invention was identified from the above properties as one belonging to *Pseudomonas alcaligenes*.

As is evident from the examples below, the strain has an excellent activity of decomposing aromatic compounds and haloorganic compounds, for example, it can completely decompose TCE of which concentration is as high as 30 ppm. Among *Pseudomonas alcaligenes*, no strain has been known which can aerobically decompose volatile chloroorganic compounds such as TCE before; therefore, the strain was identified as a novel strain and a deposit was made at National Institute of Bioscience and Human Technology, Agency of Industrial Science and Technology, with Deposition No. FERM P-14644 under the name of *Pseudomonas alcaligenes* KB2. Hereinafter the strain is referred to as KB2 strain.

As shown in the examples below, KB2 strain is capable of decomposing haloorganic compounds such as chloroorganic compounds, more specifically, chlorinated aliphatic compounds, trichloroethylene, dichloroethylene and so on. $KB_2$ strain is also capable of decomposing aromatic compounds such as phenol, cresol and so on, and necessarily is tolerant to these compounds. As is evident from the fact that these aromatic compounds are usually used as a disinfectant, they are harmful to many microorganisms. These aromatic compounds often exist also in liquid wastes and soil as pollutants, but they cannot kill KB2 strain nor inhibit the decomposing activity. Thus strain KB is capable of decomposing aromatic compounds themselves and haloorganic compounds even under the presence of such aromatic compounds.

Furthermore, $KB_2$ strain can grow at a temperature as high as 42° C., as mentioned in the paragraph related to microbiological properties, this means that with this strain, it is possible to conduct decomposition of aromatic compounds and haloorganic compounds under such a high temperature condition, where almost all strains other than KB2 strain will perish. Accordingly, a highly efficient decomposition of aromatic compounds and haloorganic compounds can be achieved simply by raising the temperature of the environment to be treated such as liquid wastes and waste water, so as to control other miscellaneous bacteria's growth and make KB2 strain a dominant species.

As the nutrient source of the medium used to culture KB2 strain of the present invention, any ordinary carbon source, nitrogen source, and inorganic salt required for microbial growth can be used so long as they are assimilable to KB2 strain. For example, M9 medium supplemented with a small amount of yeast extract is applicable.

The following is the composition of M9 medium.
$Na_2HPO_4$: 6.2 g
$KH_2PO_4$: 3.0 g
NaCl: 0.5 g
$NH_4Cl$: 1.0 g ( in 1 liter medium; pH 7 )

The culture can be carried out under an aerobic condition, and both liquid culture and solid culture are applicable. Desirably, the culture temperature is about 30° C.

Any mutants of the present strain, whether they are obtained spontaneously or artificially, are included in the scope of the present invention, so long as they have a good activity of decomposing at least one of aromatic compounds and haloorganic compounds.

According to the present invention, the decomposition of volatile chloroorganic compounds is conducted by bringing in contact KB2 strain with aromatic compounds and haloorganic compounds present in the polluted medium such as liquid wastes. The contact of the microorganism with aromatic compounds and haloorganic compounds can be carried out by culturing the microorganism in a polluted medium containing the above compounds, or by adding the above aqueous medium to the culture system of the microorganism. Batch method, semi-continuous method and continuous method, for example, are applicable. The microorganism can be utilized in a semi-solid state or in a state immobilized to a suitable carrier. If necessary, the object of decomposition treatment, for example, liquid wastes, soil and air may be subjected to other treatments, for example, adjustment of concentrations of aromatic compounds and haloorganic compounds contained, pH adjustment, supplement of nutrients and so on. Preferably, the concentration of volatile organic compounds in the decomposition treatment area is 10 ppm or less. The concentration of aromatic compounds in the treatment area is preferably 600 ppm or less, and is 400 ppm or less more preferably.

According to the present invention, the decomposition of aromatic compounds and haloorganic compounds existing in gas phase can be conducted by the contact of the above KB2 strain with the gas. Several embodiments are shown below, but are not intended to limit thereto.

According to one embodiment of the present invention, first, KB2 strain is cultured in a culture tank, and then gas polluted with aromatic compounds and haloorganic compounds is introduced into the tank at a fixed flow rate for decomposition treatment. No restrictions are placed on how to introduce the gas, however it is preferable to introduce the gas so as to agitate the culture fluid to accelerate its aeration. Introduction and discharge of the gas may be carried out continuously, or it may be carried out intermittently according to the decomposition capacity, or batch method may be employed. Preferably, such control is systematized in connection with the concentration of aromatic compounds and haloorganic compounds to obtain optimum results.

According to another embodiment of the present invention, first, KB2 strain is adhered to a carrier like soil particles, after that the reaction tank is filled with the carrier, and then gas polluted with aromatic compounds and haloorganic compounds is introduced into the tank for decomposition treatment. In addition to soil particles, any carrier can be used here, preferably those having an excellent retention of microorganisms and not interfering gas permeability. For example, applicable are various carriers for microorganisms used in bioreactors of the drug manufacturing industry, the food industry, the waste water treatment systems and so on, because they provide suitable habitats for microorganisms. More particularly, inorganic particle carriers, such as porous glass, ceramics, metal oxides, activated carbon, kaolinite, bentonite, zeolite, silica gel, alumina and anthracite; gel carriers such as starch, agar, chitin, chitosan, polyvinyl alcohol, alginic acid, polyacrylamide, carrageenan and agarose; ion-exchange cellulose; ion-exchange resins; cellulose derivatives; glutaric aldehyde; polyacrylic acid; polyurethane; polyester; and so on. The natural products, for example, cotton, hemp, paper, etc. which contain cellulose; wood powder, bark, etc. which contain lignin; are also applicable.

As mentioned above, the common culture media used for culturing microorganisms are applicable to the present invention as the materials supporting the growth of the present strain. For example, bouillon medium, M9 medium, 2×YT medium, L medium, and a medium comprised of polypeptone, yeast extract, etc. arbitrarily mixed with a carbon source like glucose, are advantageously used. These media can be in a liquid state, or in a gel state with agarose added.

As materials which can both retain the cells of present strain and supply them with nutrition, many examples can be given from among the compost used in the agriculture, forestry and fisheries and related industries. Specifically, dried materials from plants, such as straw of grains, sawdust, rice bran, bean curd lees, bagasse and so on, and seafood wastes, such as shells of crab and lobster and so on are applicable.

In clarification of gas polluted with aromatic compounds and haloorganic compounds, the cells may be introduced after the carrier material is packed or may be precultured. To make the decomposition reaction efficient, it is preferable to control the above-mentioned nutrients, water content, oxygen concentration, etc. to desirable conditions. The ratio of the carrier to water in a reaction vessel may be determined considering the microorganism's growth and aeration. The shape of the vessel may be selected considering the amount and concentration of the gas treated, preferably it is selected to enhance the contact of the gas with the microorganism retained by the carrier. For example, column, tube, tank and box type are applicable. Such a vessel may be united with an exhaust duct and a filter, and a plural vessels may be connected according to the capacity.

Polluted gas may be sometimes adsorbed by the carrier material and in a rare occasion, the effect of microbial treatment cannot be observed in the beginning of the reaction. After a certain period of time, however, the pollutant molecules adhered to the carrier material is decomposed, and other pollutant molecules are adsorbed on the surface of the material. Thus, the adsorbing ability of the material is regenerated. The capacity of removing pollutant is not saturated and constant decomposition can be expected.

All known natural strains having an activity of decomposing aromatic compounds and haloorganic compounds (for example, halogenated aliphatic compounds, such as TCE, DCE, vinyl chloride and so on), except those artificial mutants, are preferably used with an inducer in order to express their decomposing activity. An enzyme or enzymes are induced by the inducer, to decompose the inducer and then the enzyme can decompose the target aromatic compounds and haloorganic compounds. For example, methane is the inducer for *Methylosinus trichosporium* OB3b and some aromatic compounds like phenol, are the inducers for *Pseudomonas cepacia* KK01. KB2 strain is of a type whose inducer is aromatic compounds, and examples of the inducer includes aromatic compounds, such as phenol, m-cresol and p-cresol etc. Accordingly, when aromatic compounds and volatile chloroorganic compounds are decomposed with KB2 strain, it is preferable to use an inducer so that the cells of KB2 strain are expressing enzyme(s). The strain may be cultivated in the presence of an inducer before starting decomposition of aromatic compounds and haloorganic compounds, or it may be cultivated in the presence of aromatic compounds and haloorganic compounds together with the inducer. Preferably, concentration of the inducer is 10–100 ppm, more preferably 50–100 ppm.

By KB2 strain, most of the inducers are converted into an easily decomposable substances, which are completely decomposed when they are maintained in contact with ordinary soil microorganisms, or passed through a liquid waste processing vessel.

The process of the present invention is applicable to any decomposition treatment system for liquid wastes, soil and air, whether it is an open system or a closed system. In addition, in the process of the present invention, the microorganism may be immobilized to the carrier or various methods for promoting the microbial growth may be employed.

Hereinbelow the present invention will be explained in more detail with reference to the following examples.

EXAMPLE 1

Decomposition of phenol using KB2 strain

A colony of KB2 strain on an agar medium was inoculated into 200 ml of M9 medium supplemented with 0.2% of yeast extract in a Sakaguchi flask (a flat bottom flask with shoulder), and shaking culture was conducted at 30° C. for 24 hours.

Three 0.1 ml aliquots of the above culture were inoculated into three 100 ml Sakaguchi flasks containing 50 ml of M9 medium supplemented with 0.1% yeast extract and phenol at 200 ppm, 400 ppm and 600 ppm respectively, followed by shaking culture at 30° C. Then quantitative analysis of phenol was done periodically using a spectrophotometer to determine the residual phenol concentration. The results are shown in FIG. 1.

Within 13, 20 and 45 hours, 200 ppm, 400 ppm and 600 ppm of phenol were completely decomposed respectively.

EXAMPLE 2

Decomposition of cresol using KB2 strain

Two aliquots (0.1 ml) of the above culture were inoculated into two 100 ml Sakaguchi flasks containing 50 ml of M9 medium supplemented with 0.1% yeast extract where the first flask contained 100 ppm m-cresol and the second flask 100 ppm p-cresol. Then shaking culture was carried out at 30° C.

Figure 2:
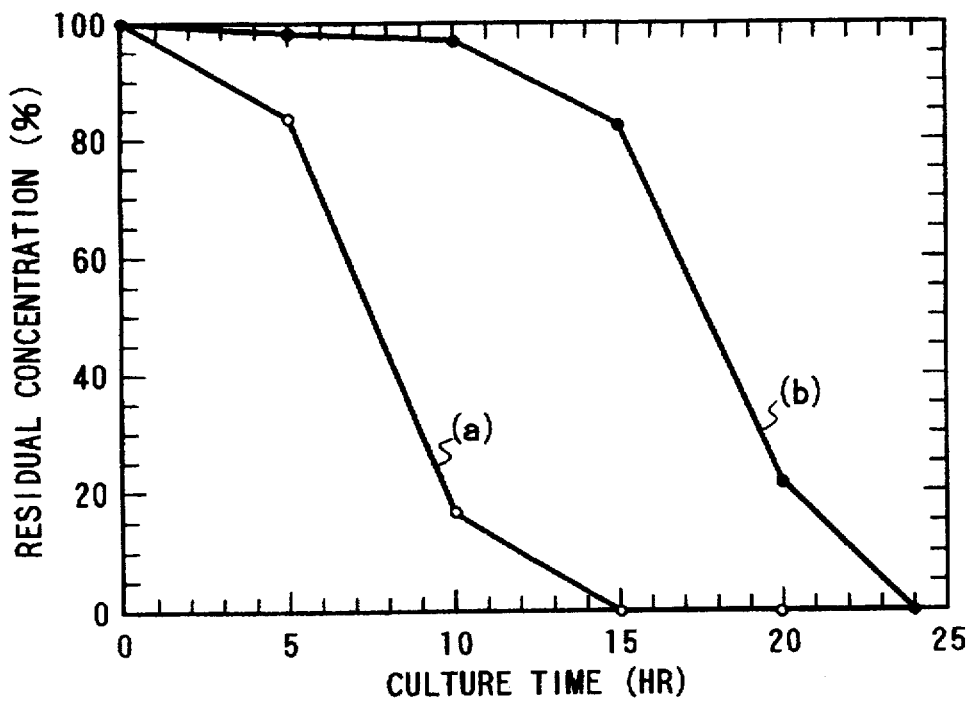
FIG. 2 is a graph showing the relation between the culture period and the concentration of cresol in the presence of KB2 strain: the curves (a) and (b) show p-cresol concentration and m-cresol concentration, respectively.

Thus the cresol decomposition experiment using KB2 strain was conducted. Quantitative analysis of cresol was done in the same manner as in Example 1. The results are shown in FIG. 2.

m-Cresol and p-cresol were completely decomposed within 24 and 15 hours, respectively.

EXAMPLE 3

Decomposition of TCE using KB2 strain (Initial concentration of TCE: 30 ppm, inducer: 100 ppm of phenol)

A colony of KB2 strain on an agar medium was inoculated into 200 ml of M9 medium supplemented with 0.2% of yeast extract in a Sakaguchi flask, and shaking culture was conducted at 30° C. for 24 hours.

Figure 3:
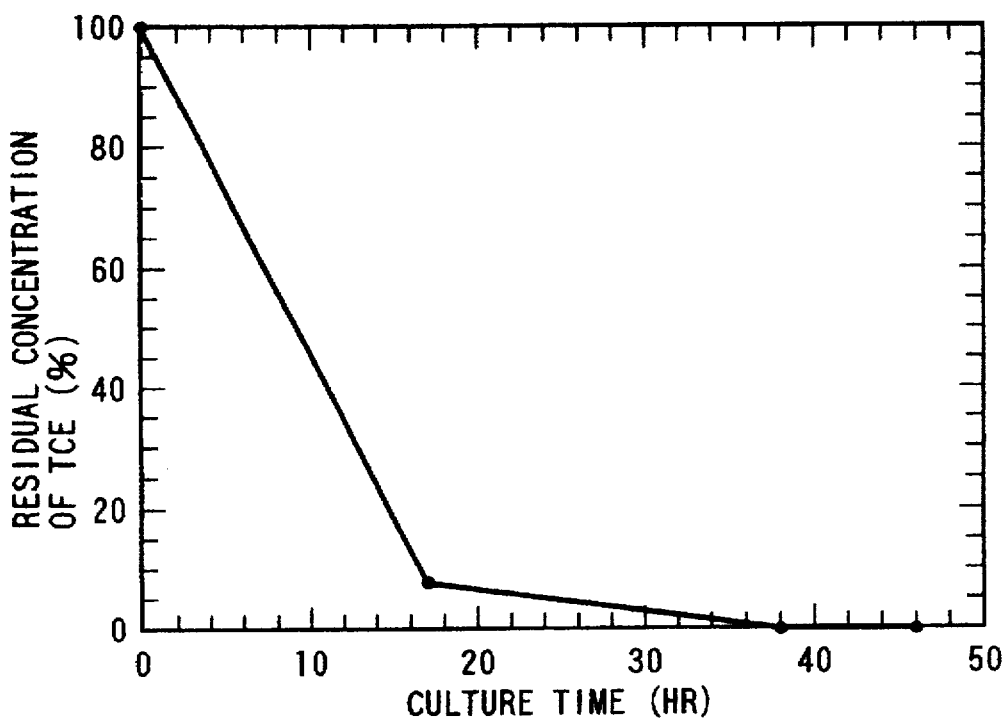
FIG. 3 is a graph showing the relation between the culture period and the concentration of TCE when KB2 strain was cultured in a culture medium containing 100 ppm of phenol (initial concentration of TCE is 30 ppm)

In a serum bottle, 5 ml of M9 medium supplemented with 100 ppm of phenol and 30 ppm of TCE in addition to 0.1% of yeast extract was placed, and a 0.1 ml aliquot of the above culture was inoculated into the medium. After the serum bottle was sealed with a butyl rubber stopper and an aluminum cap, shaking culture was conducted at 30° C. Quantitative analysis of TCE was done by gas chromatography using the head space method and the residual concentration of TCE was determined periodically. The results are shown in FIG. 3.

TCE was remarkably decomposed in the first 17 hours, and 30 ppm of TCE was completely decomposed after 38 hours. Quantitative analysis of phenol was also done at this point using a spectrophotometer to found that phenol was completely decomposed.

EXAMPLE 4

Decomposition of TCE using KB2 strain at 42° C. (Initial concentration of TCE: 10 ppm, inducer: 100 ppm of phenol)

Figure 4:
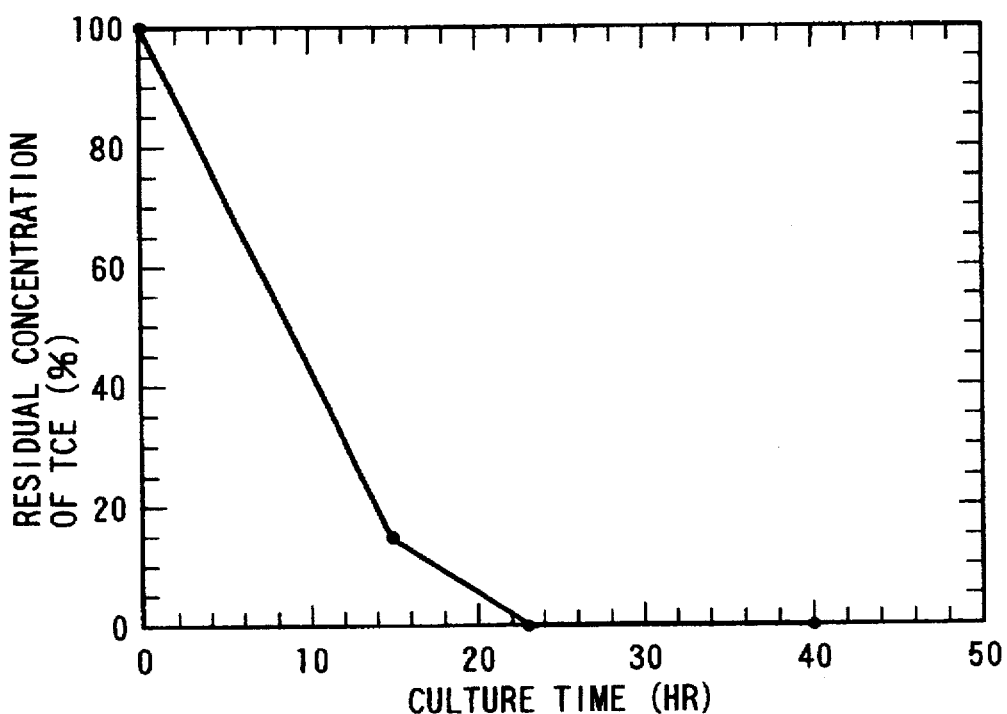
FIG. 4 is a graph showing the relation between the culture period and the concentration of TCE in the presence of KB2 strain at 42° C. (initial concentration of TCE is 10 ppm)

The same procedure as in Example 3 was conducted except that the TCE concentration of the medium was changed from 30 ppm to 10 ppm, and the temperature to 42° C. The residual TCE concentration was determined periodically. The results are shown in FIG. 4.

Decomposition of TCE remarkably progressed in the first 15 hours, and 10 ppm of TCE was completely decomposed after 23 hours. Quantitative analysis of phenol was also done at this point using a spectrophotometer, and it was found that phenol was completely decomposed.

EXAMPLE 5

Decomposition of TCE using KB2 strain (inducer: 100 ppm of m-cresol/p-cresol)

Figure 5:
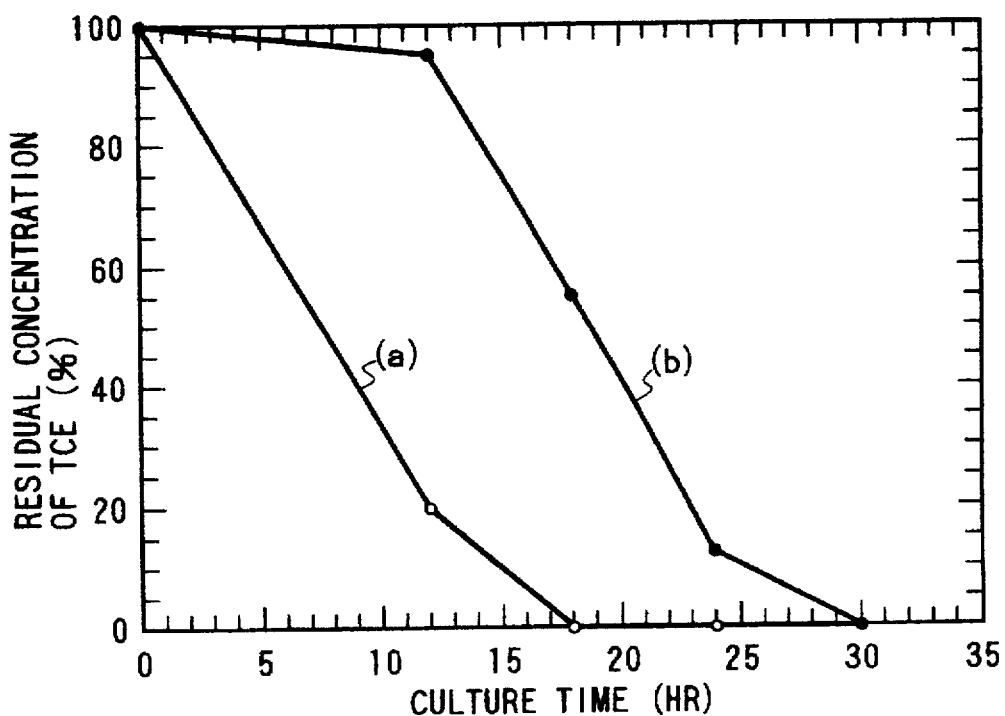
FIG. 5 is a graph showing the relation between the culture period and the concentration of TCE when KB2 strain was cultured in a culture medium containing cresol (initial concentration of TCE is 5 ppm): the curves (a) and (b) show the p-cresol concentration and m-cresol concentration, respectively.

The same procedure as in Example 3 was conducted except that the inducer was changed from 100 ppm of phenol to 100 ppm of m-cresol or p-cresol and TCE concentration of each medium was changed from 30 ppm to 5 ppm. The residual TCE concentration was determined periodically. The results are shown in FIG. 5.

In the culture system using p-cresol as an inducer, TCE was remarkably decomposed in the first 12 hours, and 5 ppm of TCE was completely decomposed after 18 hours. Quantitative analysis of p-cresol was done at this point using a spectrophotometer to confirm that p-cresol was completely decomposed. In the culture system using m-cresol as an inducer, remarkable decomposition of TCE started after about 12 hours of induction period and 5 ppm of TCE was completely decomposed after 30 hours. Quantitative analysis of m-cresol was done at this point using a spectrophotometer, and it was found that m-cresol was completely decomposed.

EXAMPLE 6

Decomposition of DCE using KB2 strain (inducer: 100 ppm of phenol)

Figure 6:
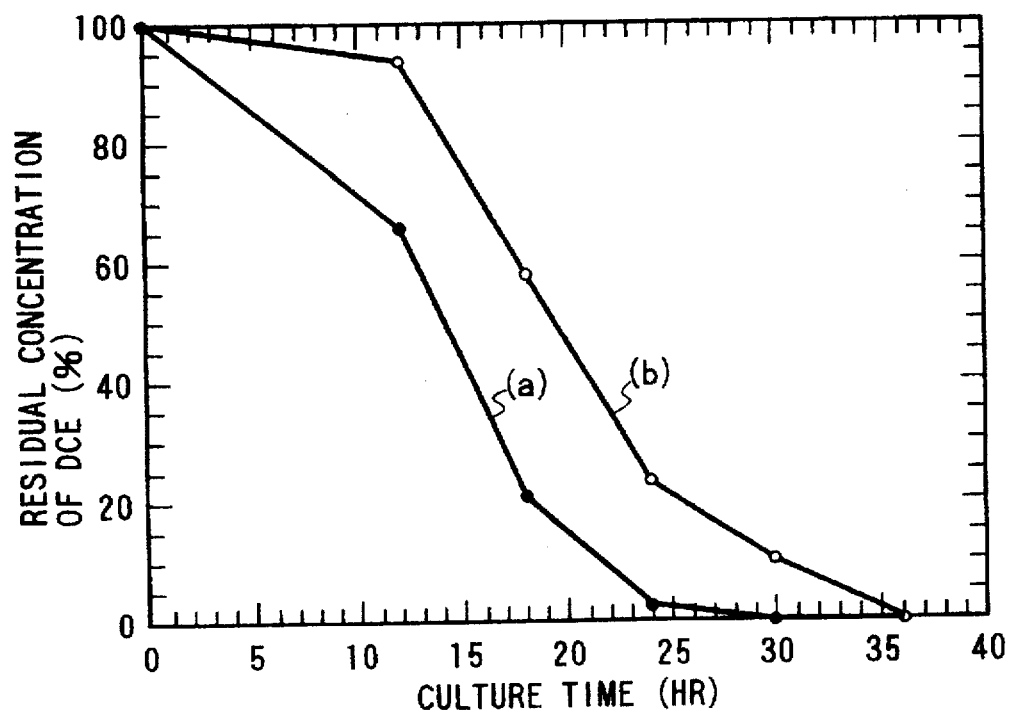
FIG. 6 is a graph showing the relation between the culture period and the concentration of DCE when KB2 strain was cultured in a culture medium containing 100 ppm of phenol (initial concentration of DCE is 10 ppm): the curves (a) and (b) represent the cis-DCE concentration and trans-DCE concentration, respectively.

The same procedure as in Example 3 was conducted except that 10 ppm of cis-1, 2-dichloroethylene (cis-1, 2-DCE) or 10 ppm of trans-1, 2-dichloroethylene (trans-1, 2-DCE) was used instead of 30 ppm of TCE, and the residual DCE concentration was determined periodically. The results are shown in FIG. 6.

cis-1, 2-DCE was remarkably decomposed in the first 18 hours and 10 ppm of cis-1, 2-DCE was completely decomposed after 30 hours. Remarkable decomposition of trans-1, 2-DCE started about 12 hours and 10 ppm of trans-1, 2-DCE was completely decomposed after 36 hours. Quantitative analysis of phenol was done at this point using a spectrophotometer, and it was found that phenol was completely decomposed.

EXAMPLE 7

Decomposition treatment of phenol in soil using KB2 strain (brown forest soil)

A colony of KB2 strain on an agar medium was inoculated into 200 ml of M9 medium supplemented with 0.2% of yeast extract in a Sakaguchi flask, and shaking culture was carried out at 30° C. for 36 hours.

Figure 7:
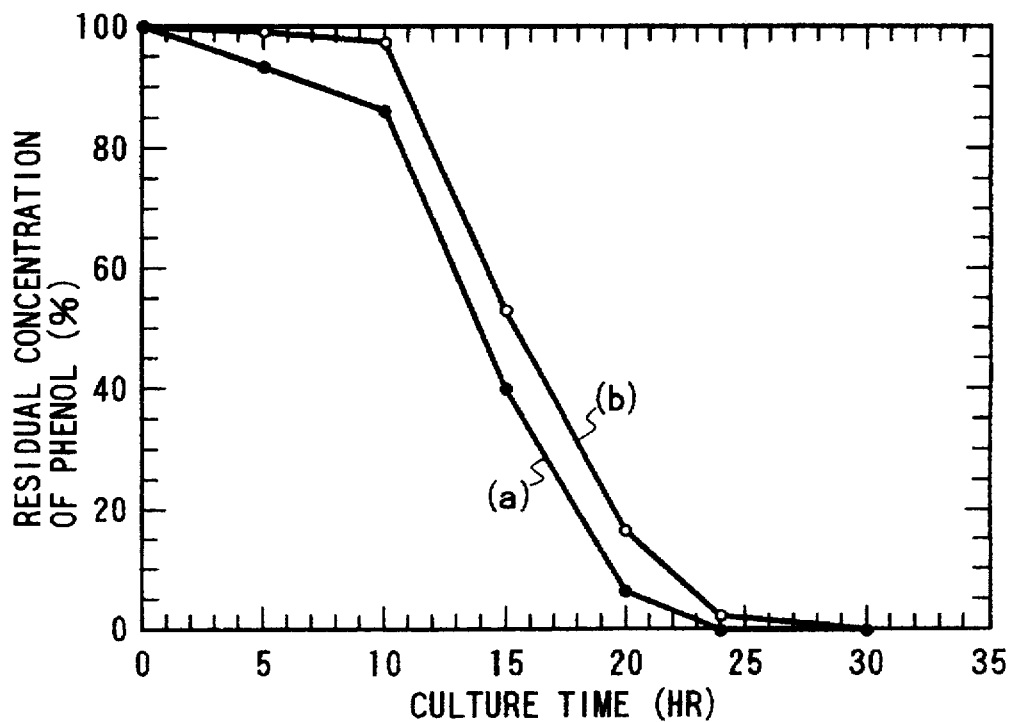
FIG. 7 is a graph showing the relation between the culture period and the concentration of phenol in brown forest soil in the presence of KB2 strain: the curves (a) and (b) represent the phenol concentration with initial concentrations 200 ppm and 400 ppm, respectively.

Two serum bottles containing 1 ml of M9 medium supplemented with 0.1% of yeast extract was prepared, and one of the bottles contained phenol at 200 ppm and the other contained phenol at 400 ppm. To each bottle, 4 g of brown forest soil was added and then a 0.1 ml aliquot of the above culture was inoculated. The bottles were stoppered with a cotton-plug and incubated stationarily at 30° C. Quantitative analysis of phenol was done in accordance with the JIS detection method using aminoantipyrine (JIS K 0102-1993, 28.1), and the residual TCE concentration was determined periodically. The results are shown in FIG. 7.

Both 200 ppm of phenol and 400 ppm of phenol were completely decomposed in 24 hours and in 30 hours respectively.

EXAMPLE 8

Decomposition treatment of cresol in soil using KB2 strain (brown forest soil)

Figure 8:
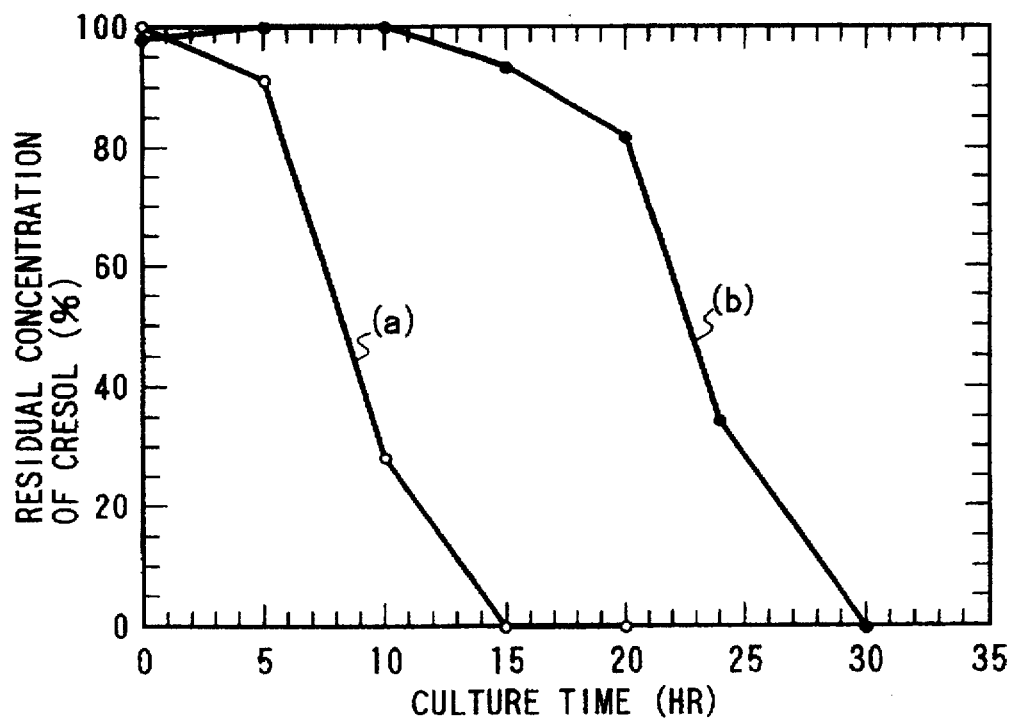
FIG. 8 is a graph showing the relation between the culture period and the concentration of cresol in brown forest soil in the presence of KB2 strain: the curves (a) and (b) represent the p-cresol concentration and m-cresol concentration, respectively.

Decomposition of cresol was attempted in the same manner as in Example 7 except that 100 ppm of m-cresol or 100 ppm of p-cresol was substituted for phenol. Quantitative analysis of cresol was done in accordance with the JIS detection method using p-hydrazidebenzenesulfonic acid (JIS K 0102-1993, 28.2), and the residual cresol concentration was determined periodically. The results are shown in FIG. 8.

Both 100 ppm of m-cresol and 100 ppm of p-cresol were completely decomposed in 30 hours and in 15 hours, respectively.

EXAMPLE 9

Decomposition treatment of TCE in soil using KB2 strain (brown forest soil)

A colony of KB2 strain on an agar medium was inoculated into 200 ml of M9 medium supplemented with 0.2% yeast extract in a Sakaguchi flask, and shaking culture was conducted at 30° C. for 36 hours.

Figure 9:
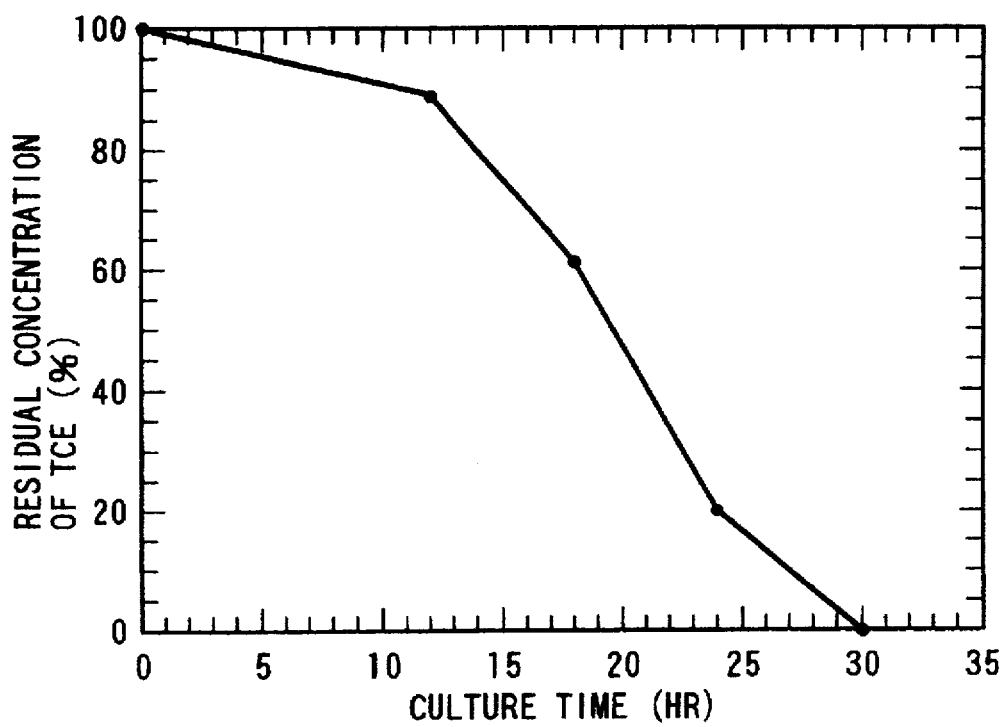
FIG. 9 is a graph showing the relation between the culture period and the residual concentration of TCE in brown forest soil in the presence of KB2 strain.

In a serum bottle containing 1 ml of M9 medium supplemented with 20 ppm of TCE and 200 ppm of phenol as well as 0.1% of yeast extract, 4 g of brown forest soil was placed, to which 0.1 ml of the above culture was inoculated. After sealing the bottle with a butyl rubber stopper and an aluminum cap, the bottle was incubated stationarily at 30° C. Quantitative analysis of TCE was done by gas chromatography using the head space method and the residual TCE concentration was determined periodically. The results are shown in FIG. 9.

TCE was remarkably decomposed after about 12 hours of induction period, and 20 ppm of TCE was completely decomposed in 30 hours. Quantitative analysis of phenol was done at this point in accordance with the JIS detection method using aminoantipyrine (JIS K 0102- 1993, 28.1), and no phenol was detected.

EXAMPLE 10

Decomposition treatment of TCE in soil using KB2 strain (loam soil)

Figure 10:
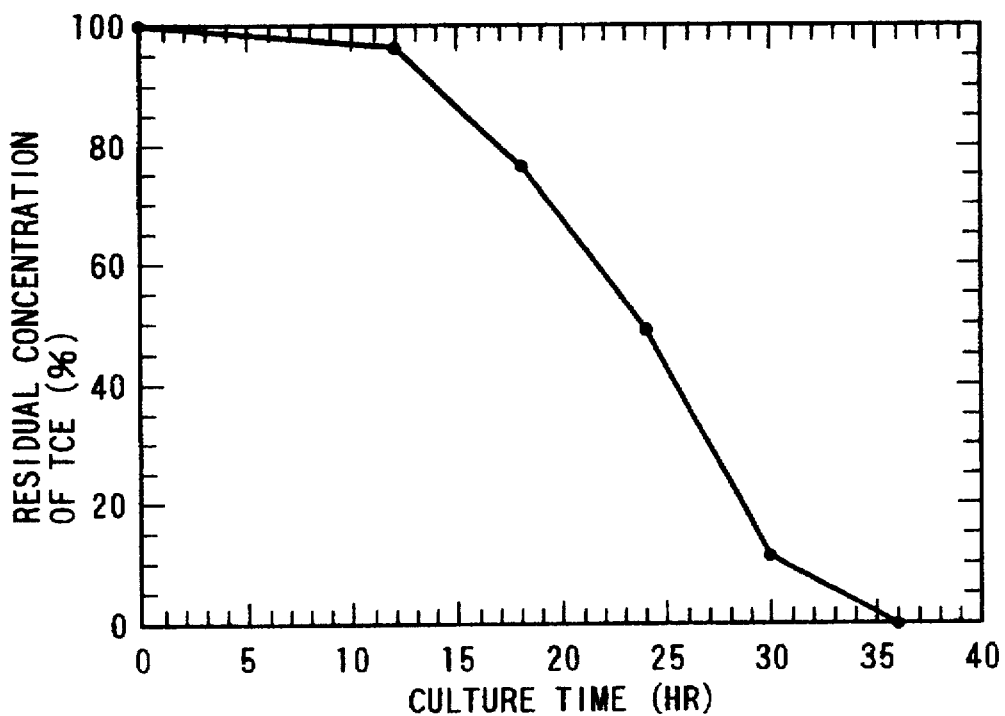
FIG. 10 is a graph showing the relation between the culture period and the concentration of TCE in loam soil in the presence of KB2 strain.

The same procedure as in Example 9 was followed except that loam soil was used in place of brown forest soil, and the residual TCE concentration was determined periodically. The results are shown in FIG. 10.

Decomposition of TCE gradually progressed after about 12 hours of the induction period, and 20 ppm of TCE was completely decomposed after 36 hours. Quantitative analysis of phenol was done at this point in accordance with the JIS detection method using aminoantipyrine (JIS K 0102-1993, 28.1), and no phenol was detected.

EXAMPLE 11

Decomposition treatment of TCE in soil using KB2 strain (fine sand)

Figure 11:
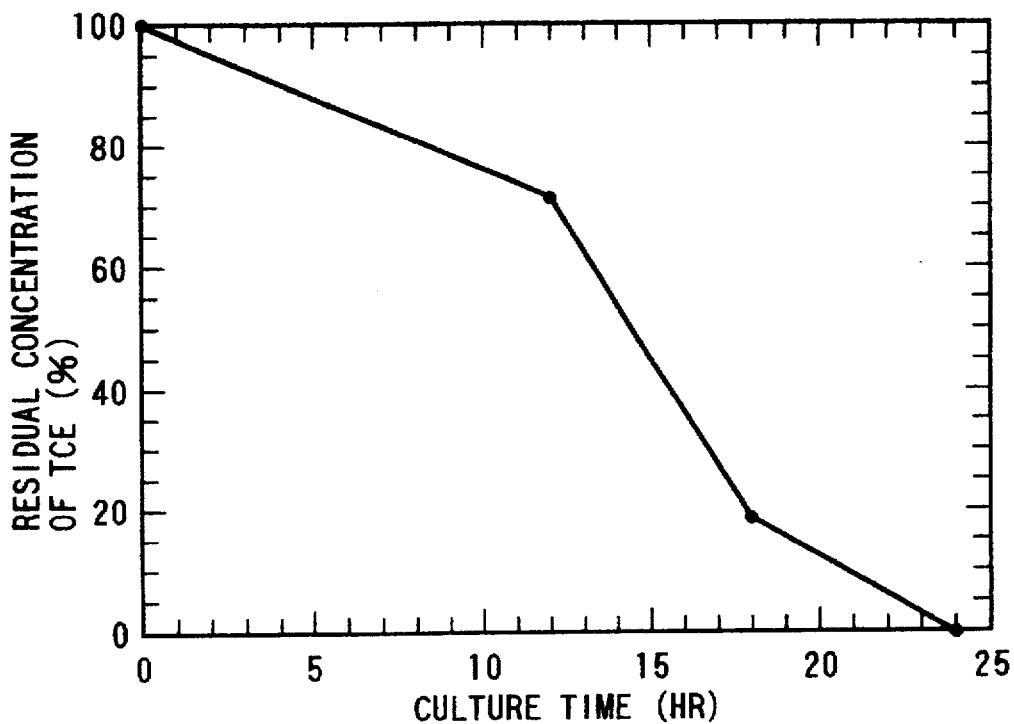
FIG. 11 is a graph showing the relation between the culture period and the concentration of TCE in fine sand in the presence of KB2 strain.

The same procedure as in Example 9 was repeated except that fine sand (silt content: about 10%) was used instead of brown forest soil, and the residual TCE concentration was determined periodically. The results are shown in FIG. 11.

Decomposition of TCE remarkably progressed in the first 18 hours, and 20 ppm of TCE was completely decomposed after 24 hours. Quantitative analysis of phenol was done at this point in accordance with the JIS detection method using aminoantipyrine (JIS K 0102-1993, 28.1), and no phenol was detected.

EXAMPLE 12

Decomposition of TCE in soil using KB2 strain (inducer: 100 ppm of p-cresol/m-cresol)

Figure 12:
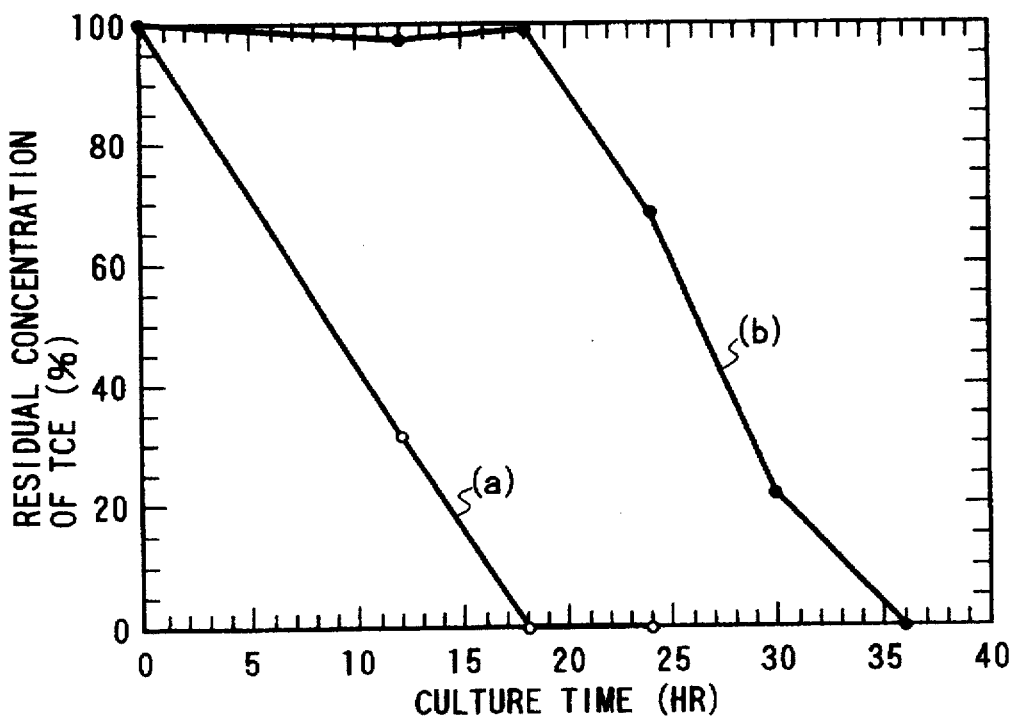
FIG. 12 is a graph showing the relation between the culture period and the concentration of TCE in brown forest soil in the presence of KB2 strain and cresol: the curves (a) and (b) represent the TCE concentrations in the presence of KB2 strain and in the presence of p-cresol and m-cresol, respectively.

The same procedure as in Example 9 was repeated except that TCE concentration was changed to 10 ppm and 100 ppm of p-cresol or m-cresol was used in place of phenol. The residual TCE concentration was determined periodically. The results are shown in FIG. 12.

In the culture system with m-cresol, TCE was remarkably decomposed after about 18 hours of the induction period, and 10 ppm of TCE was completely decomposed after 36 hours. In the culture system with p-cresol, decomposition of TCE remarkably progressed in the first 12 hours, and 10 ppm of TCE was completely decomposed after 18 hours. Quantitative analyses of p-cresol and m-cresol were done at this point in accordance with the JIS detection method using p-hydrazidebenzenesulfonic acid (JIS K 0102-1993, 28.2), and no cresol was detected.

EXAMPLE 13

Decomposition of DCE in soil using KB2 strain

Figure 13:
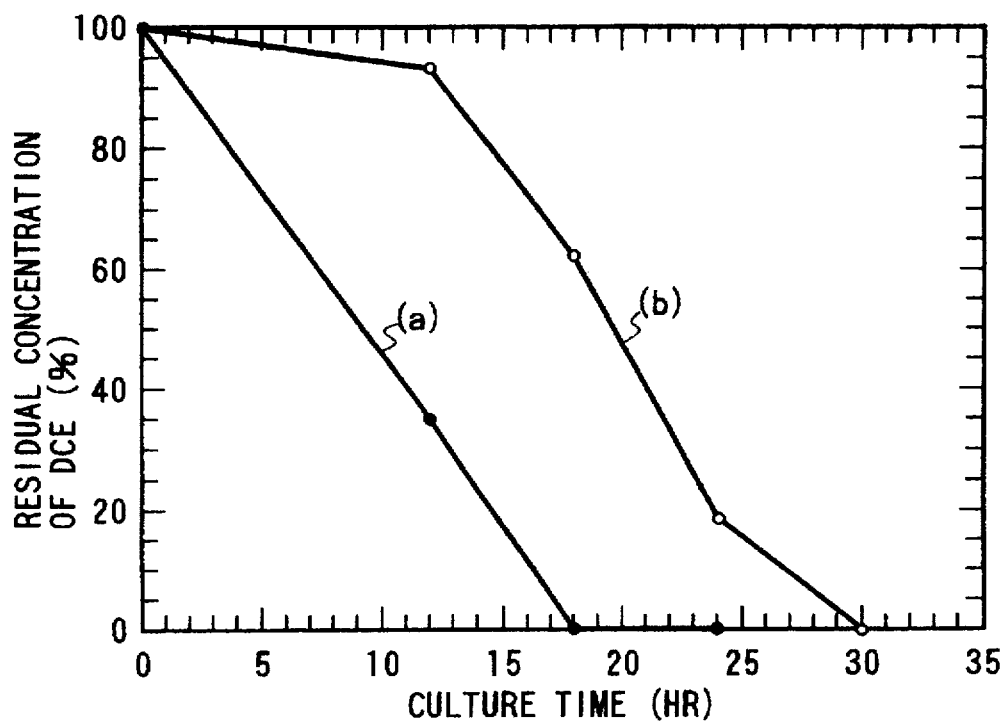
FIG. 13 is a graph showing the relation between the culture period and the concentration of DCE in brown forest soil in the presence of KB2 strain: the curves (a) and (b) show the change of the cis-DCE concentration and that of trans-DCE concentration, respectively.

The same procedure as in Example 9 was followed except that 5 ppm of cis-1, 2-dichloroethylene (cis-1, 2-DCE) or 5 ppm of trans-1, 2-dichloroethylene (trans-1, 2-DCE) was substituted for 20 ppm of TCE, and the residual DCE concentration was determined periodically. The results are shown in FIG. 13.

cis-1, 2-DCE was remarkably decomposed in the first 12 hours and 5 ppm of cis-1, 2-DCE was completely decomposed after 18 hours. Decomposition of trans-1, 2-DCE remarkably progressed after about 12 hours of the induction period and 5 ppm of trans-1, 2-DCE was completely decomposed after 30 hours. Quantitative analysis of phenol was done at this point in accordance with the JIS detection method using aminoantipyrine (JIS K 0102-1993, 28.1), and no phenol was detected.

EXAMPLE 14

Decomposition treatment of TCE in soil using KB2 strain at 42° C.

Figure 14:
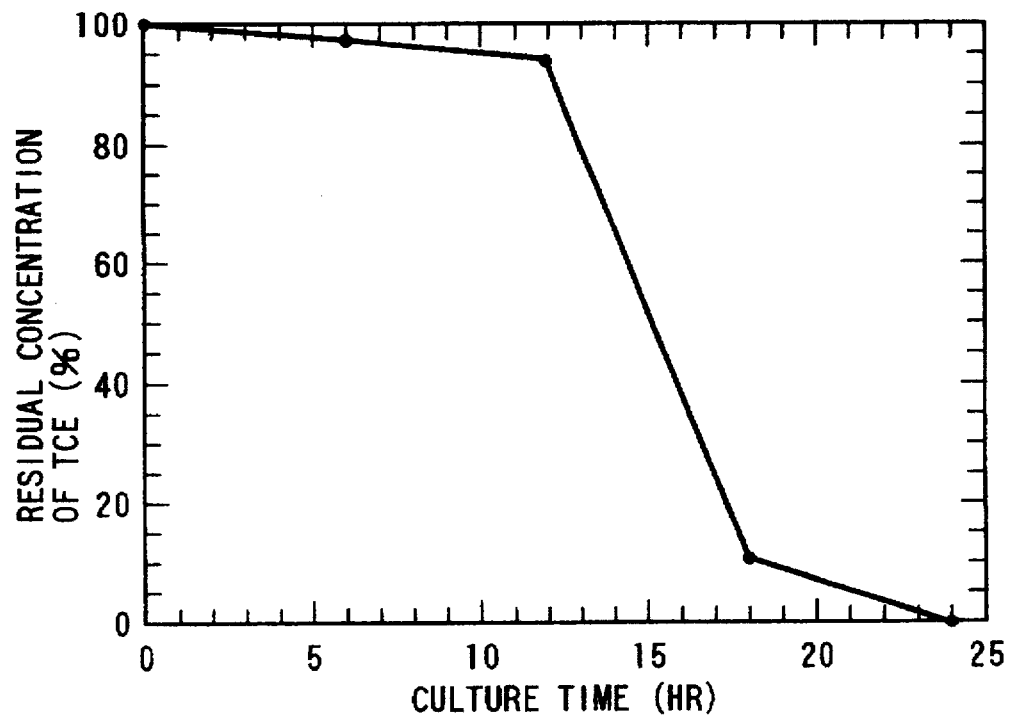
FIG. 14 is a graph showing the relation between the culture period and the concentration of TCE in brown forest soil in the presence of KB2 strain at 42° C.

The same procedure as in Example 9 was followed except that the temperature during stationary culture was changed to 42° C. and the TCE concentration to 10 ppm. The residual TCE concentration was determined periodically. The results are shown in FIG. 14.

TCE was rapidly decomposed after about 12 hours of the induction period and 10 ppm of TCE was completely decomposed after 24 hours. Quantitative analysis of phenol was done at this point in accordance with the JIS detection method using aminoantipyrine (JIS K 0102-1993, 28.1), and no phenol was detected.

EXAMPLE 15

Decomposition treatment of TCE in gas phase by aeration of KB2 strain culture (inducer: 100 ppm of phenol)

A colony of KB2 strain on an agar medium was inoculated into 200 ml of M9 medium supplemented with 0.2% of yeast extract in a Sakaguchi flask, and shaking culture was carried out at 30° C. for 36 hours.

To a 20 ml serum bottle containing 5 ml of M9 medium supplemented with 0.1% of yeast extract and 100 ppm of phenol as an inducer, 0.1 ml of the above culture was inoculated. Then the air passed through a saturated TCE solution was introduced into the above medium at a flow rate of 60 ml/min for 10 minutes. After the bottle was sealed with a butyl rubber stopper and an aluminum cap, shaking culture was conducted at 30° C. Quantitative analysis of TCE was done by gas chromatography using the head space method and the residual TCE concentration was determined periodically.

Figure 15:
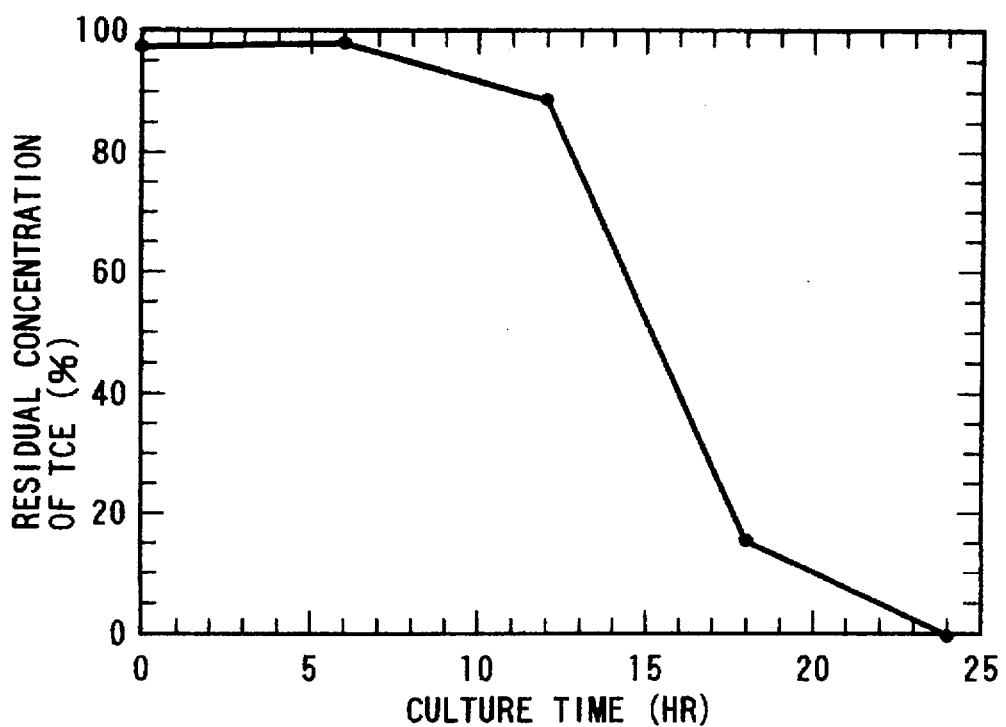
FIG. 15 is a graph showing the relation between the culture period and the concentration of TCE in gas phase when a culture medium containing phenol and KB2 strain are aerated with TCE-containing air.

A control experiment was done in the same manner as above except that the sterile medium was added instead of KB2 strain culture. The residual rate (%) of TCE to the control TCE concentration was calculated. The results are shown in FIG. 15.

Decomposition of TCE was rapidly progressed after about 12 hours of the induction period and TCE was completely decomposed after 24 hours. Quantitative analysis of phenol was done at this point in accordance with the JIS detection method using aminoantipyrine (JIS K 0102-1993, 28.1), and no phenol was detected.

EXAMPLE 16

Decomposition treatment of TCE in gas phase by aeration of KB2 strain culture (inducer: 100 ppm of p-cresol)

Figure 16:
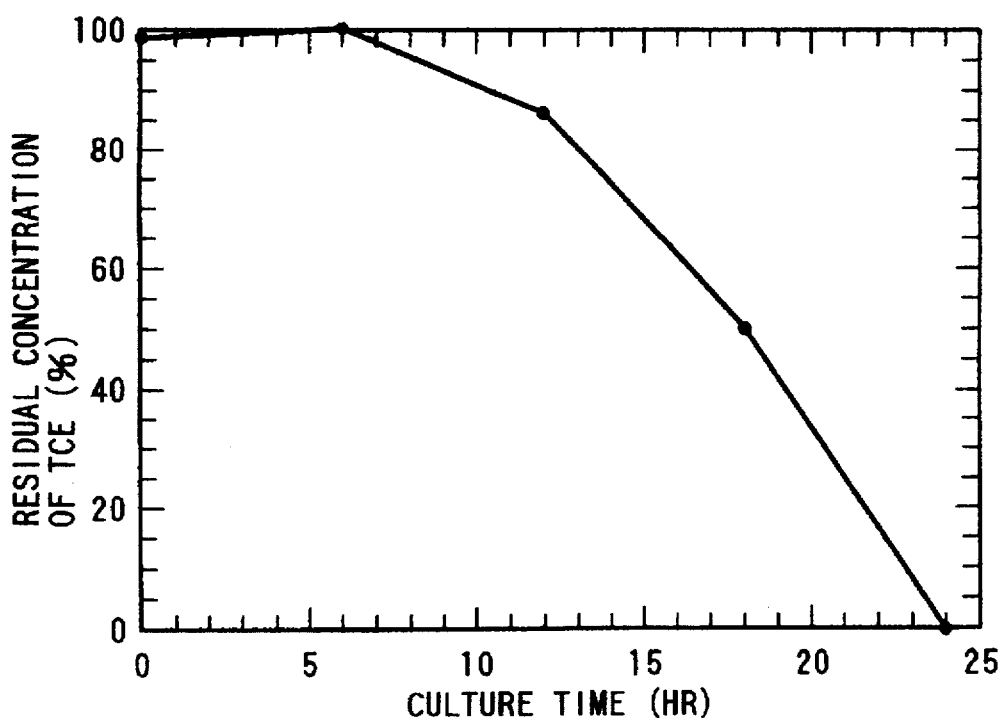
FIG. 16 is a graph showing the relation between the culture period and the concentration of TCE in gas phase when a culture medium containing KB2 strain and p-cresol was aerated with TCE-containing air.

The same procedure as in Example 15 was followed except that 100 ppm of p-cresol was substituted for 100 ppm of phenol, and the residual TCE concentration was determined periodically. The results are shown in FIG. 16.

TCE was rapidly decomposed after about 12 hours of the induction period and TCE was completely decomposed after 24 hours. Quantitative analysis of p-cresol was done at this point in accordance with the JIS detection method using p-hydrazidebenzenesulfonic acid (JIS K 0102-1993, 28.2), and no p-cresol was detected.

EXAMPLE 17

Decomposition treatment of DCE in gas phase by aeration of KB2 strain culture

Figure 17:
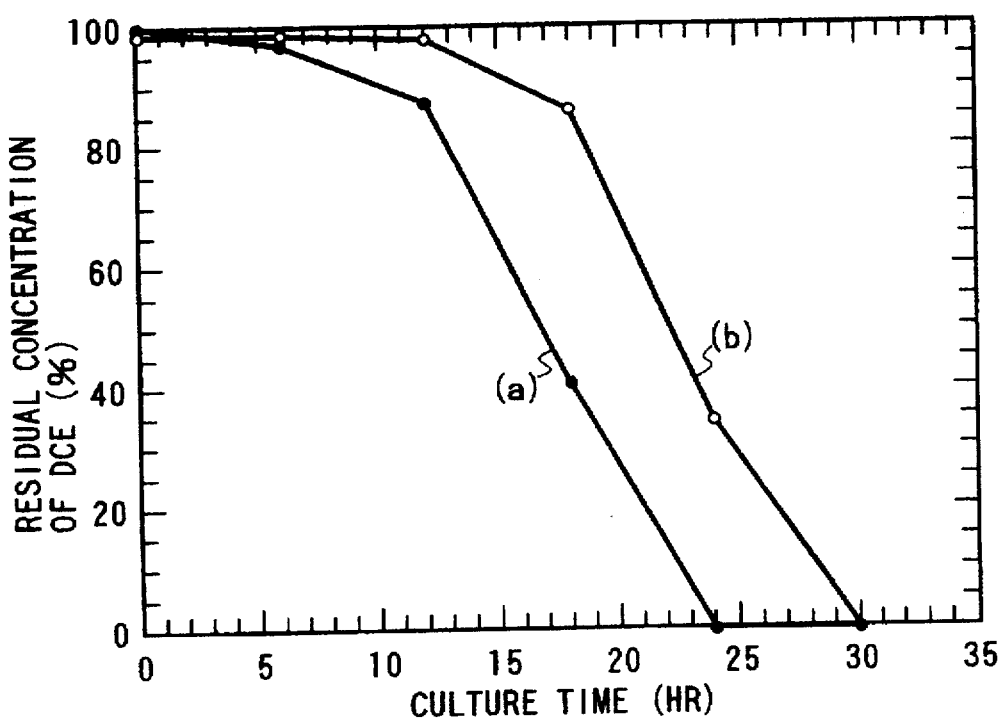
FIG. 17 is a graph showing the relation between the culture period and the concentration of DCE in gas phase when a culture medium containing KB2 strain was aerated with DCE-containing air: the curves (a) and (b) show the change of cis-DCE and trans-DCE, respectively.

The same procedure as in Example 15 was followed except that the air was passed through a saturated cis-1, 2-dichloroethylene (cis-1, 2-DCE) or trans-1, 2-dichloroethylene (trans-1, 2-DCE) solution to be introduced into the vial containing M9 medium and KB2 strain. The residual DCE concentration was determined periodically. The results are shown in FIG. 17.

Decomposition of cis-1, 2-DCE and of trans-1, 2-DCE rapidly progressed after about 12 hours of and about 18 hours of the induction periods respectively; and cis-1, 2-DCE and trans-1, 2-DCE were completely decomposed after 24 hours and after 30 hours respectively. Quantitative analysis of phenol was done at this point in accordance with the JIS detection method using aminoantipyrine (JIS K 0102-1993, 28.1), and no phenol was detected.

EXAMPLE 18

Decomposition treatment of TCE in gas phase by aeration of soil containing KB2 strain In a 20 ml serum bottle containing 5 ml of M9 medium supplemented with 0.1% yeast extract and 100 ppm phenol as an inducer, 0.1 ml of the culture of KB2 strain prepared as in Example 15 was added. Then sterilized brown forest soil was added in the bottle up to the liquid surface, and the bottle was stoppered with a butyl rubber stopper and left standing overnight at 30° C., and the surplus culture broth was removed by decantation. Then, the air passed through a saturated TCE solution was introduced into the above soil at a flow rate of 60 ml/min for 10 minutes, and the bottle was sealed with a butyl rubber stopper and an aluminum cap, followed by shaking culture at 30° C. Quantitative analysis of TCE was done by gas chromatography using the head space method and the residual TCE concentration was determined periodically.

Figure 18:
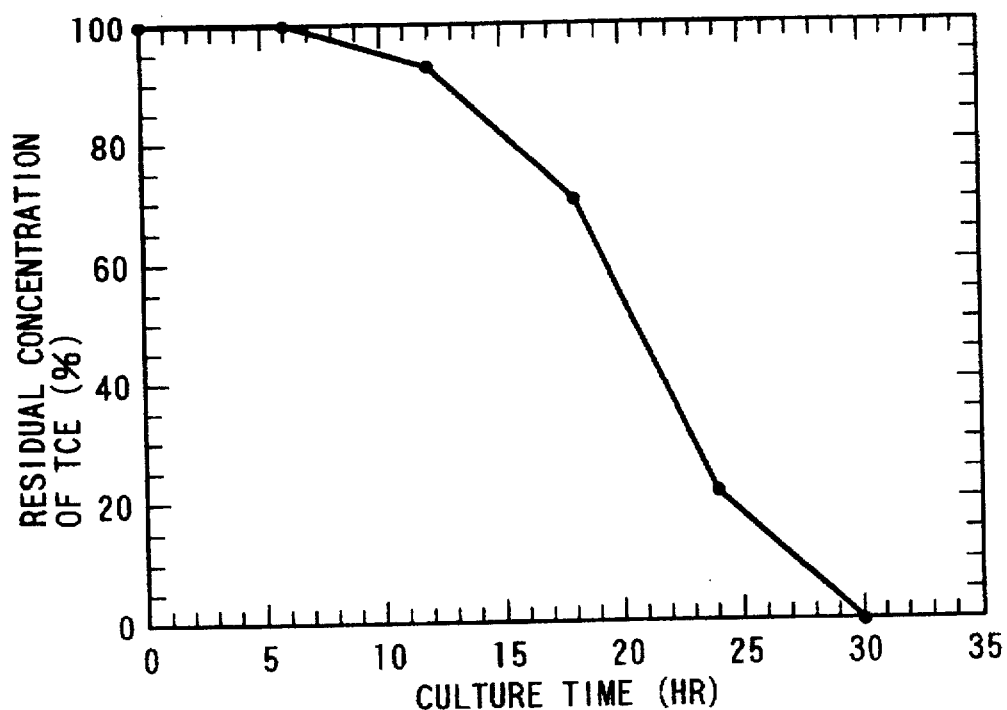
FIG. 18 is a graph showing the relation between the culture period and the concentration of TCE in gas phase when soil containing phenol-induced KB2 strain was exposed to TCE-containing air.

A control experiment was done in the same manner as above except that the sterile medium was added in place of KB2 strain culture. The residual rate (%) of TCE to the control TCE concentration was calculated. The results are shown in FIG. 18.

TCE was remarkably decomposed after about 12 hours of the induction period and TCE was completely decomposed after 30 hours. Quantitative analysis of phenol was done at this point in accordance with the JIS detection method using aminoantipyrine (JIS K 0102-1993, 28.1), and no phenol was detected.

EXAMPLE 19

Decomposition treatment of TCE in gas phase by aeration of soil containing KB2 strain (42° C.)

The same procedure as in Example 18 was followed except that after the introduction of the TCE-containing air, stationary culture at 42° C. was carried out instead of shaking culture at 30° C. The residual TCE concentration was determined periodically.

Figure 19:
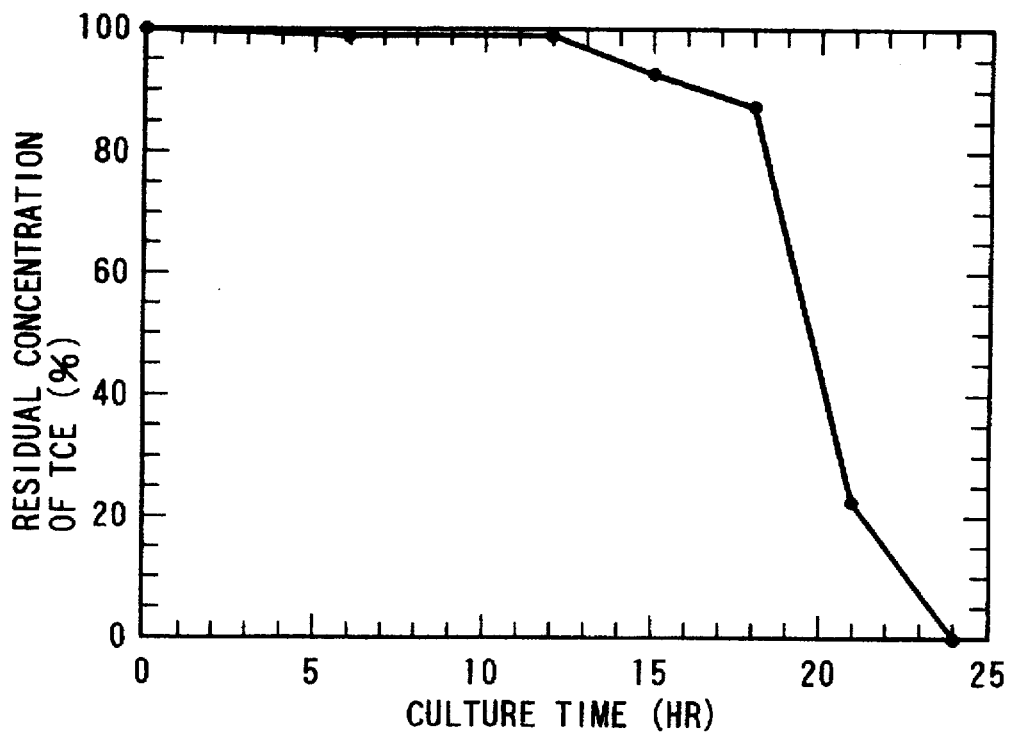
FIG. 19 is a graph showing the relation between the culture period and the concentration of TCE in gas phase when soil containing KB2 strain was exposed to TCE-containing air at 42° C.

A control experiment was done in the same manner as above except that the sterile medium was added in place of KB2 strain culture. The residual rate (%) of TCE to the control TCE concentration was calculated. The results are shown in FIG. 19.

TCE was rapidly decomposed after about 18 hours of the induction period and TCE was completely decomposed after 24 hours. Quantitative analysis of phenol was done at this point in accordance with the JIS detection method using aminoantipyrine (JIS K 0102-1993, 28.1), and no phenol was detected.

EXAMPLE 20

Decomposition treatment of TCE in gas phase by continuous aeration of KB2 strain culture In a 20 ml serum bottle containing 5 ml of M9 medium supplemented with 0.1% yeast extract and 100 ppm phenol as an inducer, 0.1 ml of the culture of KB2 strain prepared as in Example 15 was added. Then the bottle was sealed with a butyl rubber stopper and an aluminum cap, and stationary culture was carried out at 30° C. while continuously introducing the air which had been passed through a saturated TCE solution at a flow rate of 0.5 ml/min. Quantitative analysis of TCE in the effluent air was done by gas chromatography and the residual TCE concentration was determined periodically.

Figure 20:
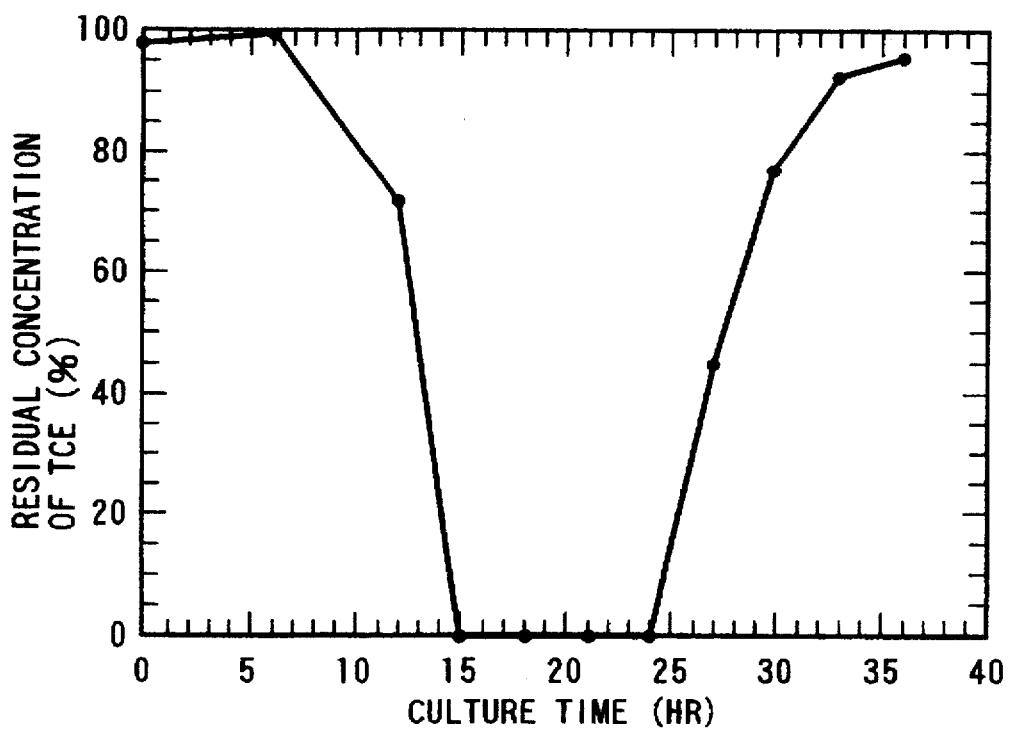
FIG. 20 is a graph showing the relation between the culture period and the concentration of TCE in gas phase when a TCE-containing air was continuously aerated into the culture of KB2 strain.

A control experiment was done in the same manner as above except that the sterile medium was added in place of KB2 strain culture. The residual rate (%) of TCE to the control TCE concentration was calculated. The results are shown in FIG. 20.

TCE was gradually decomposed after about 6 hours of the induction period and TCE was completely decomposed during the 15th–24th hour. After that, decomposition of TCE continued up to the 30th hour in total. Quantitative analysis of phenol was done at this point in accordance with the JIS detection method using aminoantipyrine (JIS K 0102-1993, 28.1), and no phenol was detected.

EXAMPLE 21

Decomposition treatment of TCE in gas phase by continuous aeration of soil containing KB2 strain The same procedure as in Example 18 was followed except that the air which had been passed through a saturated TCE solution was continuously introduced into the soil at a flow rate of 0.5 ml/min while the vial was incubated stationarily at 30° C. The residual TCE concentration was determined periodically.

Figure 21:
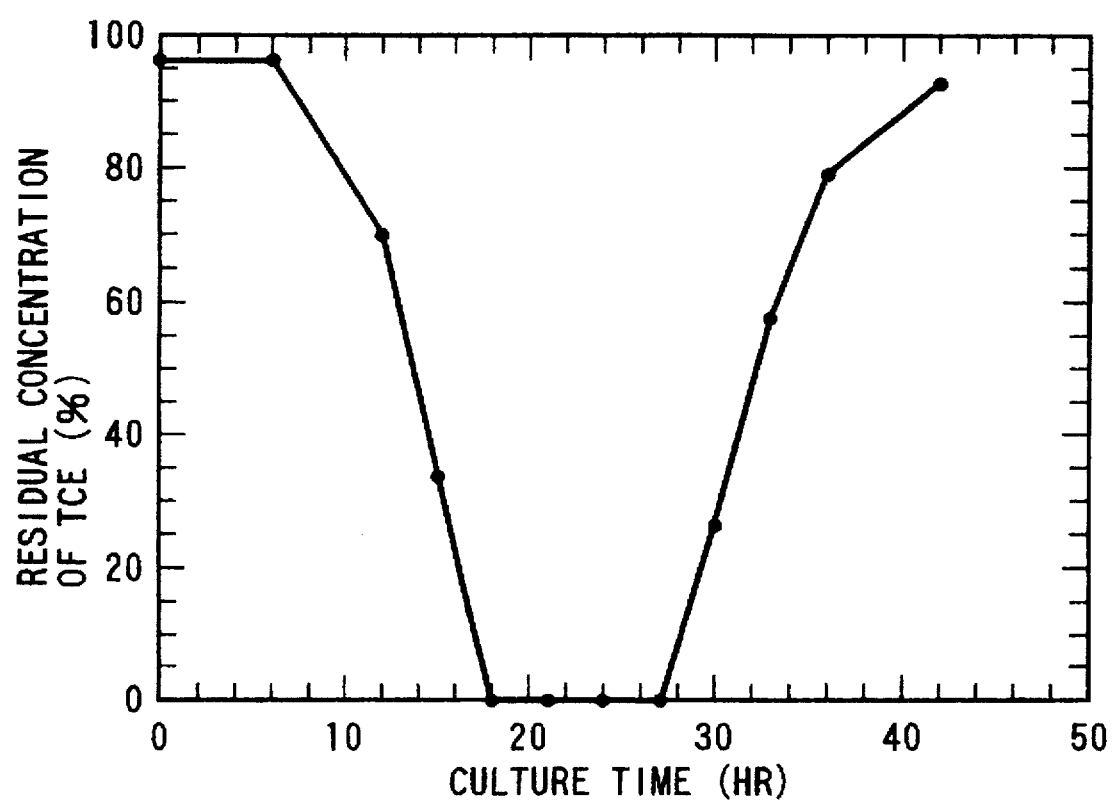
FIG. 21 is a graph showing the relation between the culture period and the concentration of TCE in gas phase when soil containing KB2 strain is continuously exposed to TCE-containing air.

A control experiment was done in the same manner as above except that the sterile medium was added in place of KB2 strain culture. The residual rate (%) of TCE to the control TCE concentration was calculated. The results are shown in FIG. 21.

Decomposition of TCE gradually started after about 6 hours of the induction period and TCE was completely decomposed during the 18th–27th hour. After that, decomposition of TCE continued till the 36th hour in total. Quantitative analysis of phenol was done at this point in accordance with the JIS detection method using aminoantipyrine (JIS K 0102-1993, 28.1), and no phenol was detected.

What is claimed is:

1. A biologically pure culture of *Pseudomonas alcaligenes* KB2, identified under Deposition No. FERM P-14644 in National Institute of Bioscience and Human Technology, Agency of Industrial Science and Technology.

* * * * *